United States Patent [19]
Arai et al.

[11] Patent Number: 5,710,179
[45] Date of Patent: Jan. 20, 1998

[54] ANTITUMOR AGENT

[75] Inventors: Shigeyuki Arai; Yasushi Nishizaki; Tetsuo Kimoto; Masashi Kurimoto, all of Okayama, Japan

[73] Assignee: Kabushiki Kaisha Hayashibara Seibutsu Kagaku Kenkyujo, Okayama, Japan

[21] Appl. No.: 675,059

[22] Filed: Jul. 3, 1996

[30] Foreign Application Priority Data

Apr. 5, 1995 [JP] Japan .................................. 7-191015

[51] Int. Cl.$^6$ .................................................. A61K 31/19
[52] U.S. Cl. .................................. 514/568; 514/570
[58] Field of Search .................................. 514/568, 570

[56] References Cited

FOREIGN PATENT DOCUMENTS

| | | |
|---|---|---|
| 0622068 A2 | 11/1994 | European Pat. Off. . |
| 60-163841 | 8/1985 | Japan . |
| 6-256177 | 9/1994 | Japan . |

OTHER PUBLICATIONS

Chemical Abstracts 124:194307 & JP 070330596 A2 (Eiken Chemical, Japan), (Dec. 19, 1995).

Patent Abstracts of Japan, vol. 18, No. 651, p. 157 and JP 060256177 (Hayashibara Biochem Lab, Inc.), Sep. 13, 1994.

Patent Abstracts of Japan, vol. 10, No. 4 [c322] [2061] and JP 600163841 (Seisan Kaihatsu KK) Aug. 26, 1995).

Chem. Pharm. Bull. 36(2), pp. 769–775 (1988) (Okuno et al).

Biosci. Biotechnol. Biochem. 58(5), pp. 945–946 (1994) (Aga et al).

Foods & Food Ingredient of Japan, No. 160, pp. 64–73, (1994) Summary Only.

Shimosato et al, Human Cancer and Nude Mice, pp. 321–323, (1982) Only p. 321, line 13 to p. 322, line 13.

Zdero et al, Phytochemistry, vol. 25, pp. 2841–2855, 1986.

Okuno et al, Chem. Pharm. Bull., 36 (2) pp. 769–775, 1988.

*Primary Examiner*—Jerome D. Goldberg
*Attorney, Agent, or Firm*—Browdy and Neimark

[57] ABSTRACT

An antitumor agent comprising as an effective ingredient 3-[4-hydroxy-3,5-bis(3-methyl-2-butenyl)phenyl]-2-propenoic acid obtained from propolis and/or its physiologically acceptable salt(s). The agent exerts a strong antitumor activity without substantially inducing side effects.

3 Claims, No Drawings

ANTITUMOR AGENT

BACKGROUND OF THE INVENTION

1. Field of the Invention

The present invention relates to an antitumor agent comprising 3-[4-hydroxy-3,5-bis(3-methyl-2-butenyl)phenyl]-2-propenoic acid and/or its physiologically acceptable salt(s) as an effective ingredient.

2. Description of the Prior Art

In the medical field of today for treating malignant tumors, doctors and researchers focus on earlier findings of and surgical excisions of malignant tumors. In the cause of malignant tumors developing on sites where their excisions are substantially difficult and the metastasis or the invasion of malignant tumors may occurring, the sites or the patients are radiated or administered with antitumor agents regularly.

In the later treatment, antitumor agents now used frequently can be roughly classified into the following types: (i) A type of using an immunopotentiating activity, (ii) a type of using a metabolic antagonizing activity, and (iii) a type of using a direct tumor killing activity. Among these types, the types (ii) and (iii), particularly, artificially produced antitumor agents exert a strong antitumor activity, but in some cases they could not be administered successively because they have serious side effects. The type (i) antitumor agents have relatively-low side effects, but are insufficient in their antitumor activity, and most of them are frequently used with other medicaments and administered to patients in the end stage, who are suffering from malignant tumors and have no other effective treatment.

SUMMARY OF THE INVENTION

The present invention relates to an antitumor agent comprising 3-[4-hydroxy-3,5-bis(3-methyl-2-butenyl)phenyl]-2-propenoic acid and/or its physiologically acceptable salt(s) as an effective ingredient.

The object of the present invention is to provide an antitumor agent which exerts a strong antitumor activity without substantial fear of causing side effects.

To overcome the above object, the present inventors energetically studied on natural extracts, particularly, antitumor substances in propolis extracts and have found that a carbonic acid, 3-[4-hydroxy-3,5-bis(3-methyl-2-butenyl)phenyl]-2-propenoic acid, and its salts exert a strong antitumor activity.

DETAILED DESCRIPTION OF THE INVENTION

Propolis extracts have long been used as a folk medicine such as an antiseptic, an anti-inflammatory agent, or an antitumor agent. Recently, a scalpel of the modern science technology has been applied to propolis extracts: For example, Shinobu MATSUDA reported in "Foods & Food Ingredients Journal of Japan", Vol.160, pp.64–73 (1994) that a novel substance, which belongs to quercetin, caffeic acid phenethyl ester, and clerodane diterpenoid, exerted an antitumor activity on human malignant tumors.

The compound, 3-[4-hydroxy-3,5-bis(3-methyl-2-butenyl)phenyl]-2-propenoic acid, which the present inventors found the existence in propolis extracts and the antitumor activity, is in itself a conventionally known compound as disclosed in Japanese Patent Laid-Open No.256,177/94, applied by the present applicant, which discloses that the compound can be isolated from propolis extracts. However, as far as the present inventors know, there is no publication that discloses and indicates the compound's antitumor activity and, therefore, the present antitumor agent containing the compound as an effective ingredient is novel.

The present antitumor agent comprising 3-[4-hydroxy-3,5-bis(3-methyl-2-butenyl)phenyl]-2-propenoic acid and/or its physiologically acceptable salt(s) as an effective ingredient exerts a strong antitumor activity on human malignant tumors. Based on the data of acute toxicity test using test animals, these compounds have an extremely low toxicity.

Now explaining the present antitumor agent in more detail, 3-[4-hydroxy-3,5-bis(3-methyl-2-butenyl)phenyl]-2-propenoic acid and its salts have the following chemical formula 1. In the formula, the symbol "X" represents a physiologically acceptable cation such as a hydrogen, sodium, potassium, calcium, magnesium or ammonium ion.

Chemical formula 1:

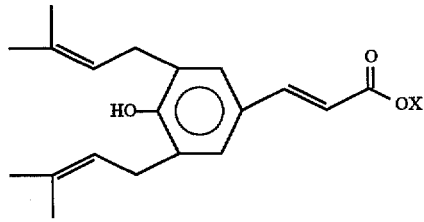

The 3-[4-hydroxy-3,5-bis(3-methyl-2-butenyl)phenyl]-2-propenoic acid and its salts used in the present invention can be prepared from natural sources or synthesized chemically. Independently of source and origin, any types of them can be used in the present invention as long as they exert the desired effect. The natural sources of 3-[4-hydroxy-3,5-bis(3-methyl-2-butenyl)phenyl]-2-propenoic acid and its salts are, for example, propolis and the leaves and stems of composites such as Artemisia capillaris. For example, Japanese Patent Laid-Open No. 256,177/94, "Phytochemistry", Vol. 25, No. 12, pp. 2,841–2,855 (1986) by C. Zdero et al, and "Chemical Pharmaceutical Bulletin", Vol. 36, No. 2, pp. 769–775 (1988) by I. Okuno et al detail methods to isolate 3-[4-hydroxy-3,5-bis(3-methyl-2-butenyl)phenyl]-2-propenoic acid from the above natural sources. The method, disclosed in Japanese Patent Laid-Open No. 163,841/85, can be arbitrarily used for chemically synthesizing 3-[4-hydroxy-3,5-bis(3-methyl-2-butenyl)phenyl]-2-propenoic acid and its salts.

Giving an outline of the isolation of 3-[4-hydroxy-3,5-bis(3-methyl-2-butenyl)phenyl]-2-propenoic acid from natural sources, propolis and the leaves and stems of composites as a material are disrupted and extracted with a solvent selected from water, organic solvents such as methanol, ethanol, acetone, diethyl ester and ethyl acetate, and mixtures thereof, followed by concentrating and purifying the extracts. The methods for concentrating and purifying the extracts used in the present invention are conventional ones used for such purposes for similar extracts: For example, salting out, dialysis, filtration, separation, separatory sedimentation, crystallization, gel filtration chromatography, ion exchange chromatography, gas chromatography, and high-performance liquid chromatography, and two or more of these techniques can be used in combination. To prepare physiologically acceptable salts of 3-[4-hydroxy-3,5-bis(3-methyl-2-butenyl)phenyl]-2-propenoic acid, hydroxides such as sodium, potassium, calcium, magnesium, and ammonium hydroxides are allowed to act on 3-[4-hydroxy-3,5-bis(3-methyl-2-butenyl) phenyl]-2-propenoic acid. Because these salts of 3-[4-hydroxy-3,5-bis(3-methyl-2-butenyl)phenyl]-2-propenoic acid more dissolve in water than intact 3-[4-hydroxy-3,5-bis(3-methyl-2-butenyl)phenyl]-2-propenoic acid, they are readily handled in the pharmaceutical preparations and administered satisfactorily to patients at a relatively high dose.

The antitumor agent as referred to in the present invention includes intact 3-[4-hydroxy-3,5-bis(3-methyl-2-butenyl) phenyl]-2-propenoic acid and/or its salt(s), as well as compositions with one or more carries, excipients, diluents, stabilizers, and biologically active substances such as interferon-α, interferon-β, interferon-γ, interleukin-2, interleukin-12, TNF-α, TNF-β, cyclophosphamide, adriamycin, α-difluoromethylornithine, melphalan, 5-fluorouracil, doxorubicin, chlorambucil, vinblastine, 1,3-bis(2-chloroethyl)-1-nitrosourea, cisplatin, levamisole, D-penicillamine, gold compounds, BCG, KRESTIN® (polysaccharide K), PICIBANIL® (OK-432), Maruyama vaccine, and lentinan.

The present antitumor agent can be prepared into an agent in a unit dose form, which contains 4- to 1/40-fold of a dose of 3-[4-hydroxy-3,5-bis(3-methyl-2-butenyl)phenyl]-2-propenoic acid and/or its salt(s) as an effective ingredient and has a physically separated- and shaped-form suitable for administration. Examples of such agents are injections, liquids, powders, granules, tablets, capsules, sublinguals, eye washes, collunaria, and suppositories. Depending on the type of the present agent, it contains usually at least 0.01% by weight of 3-[4-hydroxy-3,5-bis(3-methyl-2-butenyl) phenyl]-2-propenoic acid and/or its salt(s).

Explaining the use of the present antitumor agent, it exerts a strong antitumor activity independently of the oral or parenteral administration. Depending on the types of malignant tumors and the patients' symptoms, the present agent is administered orally or parenterally, i.e. intradermally, subcutaneously, intramuscularly, or intravenously to a patient at a dose of about 1 µg to 10 mg, preferably, about 10 µg to 1 mg, 1–4 shots per day or 1–5 shots per week while observing the patients' symptoms and the patients' conditions after the administration.

The present antitumor agent exerts a strong antitumor activity on human malignant tumors, for example, solid tumors such as colon cancer, rectum cancer, Gastric cancer, thyroid gland cancer, lingual cancer, bladder cancer, choriocarcinoma, cancer of liver, uterine cancer, prostatic cancer, pharyngeal cancer, lung cancer, breast cancer, malignant melanoma, Kaposi sarcoma, brain tumor, neuroblastoma, ovarian tumor, testicular tumor, osteosarcoma, pancreatic cancer, renal carcinoma, hypernephroma, and angioendothelioma; and hematopoietic malignant tumors such as leukemia and lymphoma.

The following experiments explain the antitumor activity and toxicity of the present antitumor agent based on the animal experiment using rodents. It is well known that the experimental system using rodents with malignant tumors is a reliable model for human malignant tumors.

Experiment 1

Preparation of 3-[4-hydroxy-3,5-bis(3-methyl-2-butenyl)phenyl]-2-propenoic acid and its salt Experiment 1-1

Preparation of 3-[4-hydroxy-3,5-bis(3-methyl-2-butenyl)phenyl]-2-propenoic acid

According to the method disclosed in Japanese Patent Laid-Open No.256,177/94, 3-[4-hydroxy-3,5-bis(3-methyl-2-butenyl)phenyl]-2-propenoic acid (hereinafter designated as "compound 1") was prepared from a propolis mass from Brazil.

153.34 parts by weight of the propolis mass was disrupted, extracted with ethyl acetate, and admixed with methanol, followed by removing the produced sediment by a centrifuge and adding methanol to the supernatant after concentration with an evaporator. The newly produced sediment in the methanol solution was removed by a centrifuge, and the supernatant was concentrated similarly as above. To the concentrate was added methanol to obtain 63.9 parts by weight of an extract.

Thirty-five parts by weight of the extract, on a dry solid basis (d.s.b.), was fed to a column packed with "SILICA GEL 60G650", commercialized by Katayama Chemical Industries, Co., Ltd, Tokyo, Japan, followed by feeding to the column with a gradient mixture solution of hexane and ethyl acetate. Fractions eluted at the concentration ratios of hexane and ethyl acetate from 59:41 to 57:43 were pooled, fed to a column packed with "SEPHADEX LH-20" commercialized by Pharmacia LKB Biotechnology AB, Uppsala, Sweden, and fed with methanol at an SV (space velocity) 0.16, followed by collecting and concentrating the fractions eluted at an elution volume of about 1.1-fold of the gel volume to obtain a crystal. The crystal was washed with hexane and dried into 0.28 part by weight of a crystalline solid.

A part of the crystalline solid was analyzed in a conventional manner on elemental analysis, mass spectrometry, ultraviolet spectroscopy, infrared spectroscopy, and nuclear magnetic resonance spectroscopy. The data was compared with that of 3-[4-hydroxy-3,5-bis(3-methyl-2-butenyl) phenyl]-2-propenoic acid, reported in "Chemical Pharmaceutical Bulletin", Vol. 36, No. 2, pp. 769–775 (1988), revealing that they coincided well. Based on these results, the crystalline solid obtained in the above procedures was identified as 3-[4-hydroxy-3,5-bis(3-methyl-2-butenyl) phenyl]-2-propenoic acid.

Experiment 1-2

Preparation of salt of 3-[4-hydroxy-3,5-bis(3-methyl-2-butenyl)phenyl]-1-propenoic acid Compound 1 obtained by the method in Experiment 1-1 was dissolved in ethanol into an about 10 w/w % ethanol solution which was then admixed with an equimolar sodium, calcium, magnesium, or potassium hydroxide, followed by concentrating and drying the solution on a centrifugal condenser to obtain a solid product. The compound 1, sodium salt of 3-[4-hydroxy-3,5-bis(3-methyl-2-butenyl)phenyl]-2-propenoic acid (hereinafter designated as "compound 2"), calcium salt of 3-[4-hydroxy-3,5-bis(3-methyl-2-butenyl) phenyl]-2-propenoic acid (hereinafter designated as "compound 3"), magnesium salt of 3-[4-hydroxy-3,5-bis(3-methyl-2-butenyl)phenyl]-2-propenoic acid (hereinafter designated as "compound 4"), or potassium salt of 3-[4-hydroxy-3,5-bis(3-methyl-2-butenyl)phenyl]-2-propenoic acid (hereinafter designated as "compound 5") was prepared into an aqueous solution with an appropriate concentration. Each aqueous solution was sterilized and filtered for use in the following animal experiments.

Experiment 2

Antitumor Activity on Mouse with Carcinoma

About $1 \times 10^6$ cells/mouse of Meth A sarcoma was intraperitoneally injected into 8-week-old BALB/c male mice.

From the next day after the administration, mice in a group of 10 were intraperitoneally injected twice a week with 0.2 ml of a physiological saline containing 0.0005, 0.005, 0.05 or 0.5 μg of any one of the compounds 1–5, and observed for 40 days. As a control, 0.2 ml/mouse/shot of physiological saline free of the compounds 1–5 was intraperitoneally injected to other groups of mice similarly as above.

Based on the data of the average day surviving (T) in the Groups of mice with the compounds 1–5 and the average day surviving (C) in the control group of mice, the prolongation percentage of life (T/C %) was calculated by the formula 1. The results were in Table 1.

Formula 1:

$$\text{The prolongation percentage of life } (T/C\,\%) = \frac{T}{C} \times 100$$

0.05 μg/mouse/shot, and the antitumor activity of the compounds 1–5 was tested by administering them at the above dose to nude mice transplanted with human malignant tumors.

As shown in Table 2, $5 \times 10^7$ cells/mouse of human malignant tumor cells were transplanted subcutaneously in the dorsal sites of 8-week-old BALB/c nude mice. Thereafter mice, observed the tumor cells' insertion, were grouped in a group of 7 mice, then administered twice a week with 0.2 ml of a physiological saline containing 0.05 μg of the compound 2 to the dorsal subcutaneous tissues, and observed for 25 days. As a control, mice in other group were administered in the same administration schedule with 0.2 ml/shot of physiological saline free of the compound 2.

On the 27th day after the transplantation, tumor masses formed in the nude mice were extracted and weighed, on a wet cell basis, according to the method as disclosed by Y. Shimosato and N. Tamaoki in "*Jingan-to-Nude-mouse*

TABLE 1

| Compound | Dose (μg/0.2 ml/mouse) | Average day surviving | Number surviving after 40 days | Prolongation percentage of life (T/C %) |
|---|---|---|---|---|
| 1 | 0.0005 | 33.5 ± 0.6 | 3 | 119.2 |
|   | 0.005  | 35.0 ± 0.9 | 5 | 124.6 |
|   | 0.05   | 37.3 ± 0.4 | 7 | 132.7* |
|   | 0.5    | 39.8 ± 0.1 | 9 | 141.6* |
| 2 | 0.0005 | 32.3 ± 0.8 | 2 | 114.9 |
|   | 0.005  | 36.5 ± 0.5 | 6 | 129.9 |
|   | 0.05   | 38.1 ± 0.1 | 8 | 135.6* |
|   | 0.5    | 40.0<     | 10 | 142.3* |
|   | 0.0005 | 31.1 ± 0.6 | 2 | 110.7 |
|   | 0.005  | 35.9 ± 0.3 | 6 | 127.8 |
|   | 0.05   | 38.9 ± 0.2 | 8 | 138.4* |
|   | 0.5    | 39.0 ± 0.2 | 9 | 138.8* |
| 4 | 0.0005 | 34.9 ± 0.3 | 3 | 124.2 |
|   | 0.005  | 35.7 ± 0.4 | 5 | 127.0 |
|   | 0.05   | 37.5 ± 0.2 | 7 | 133.5* |
|   | 0.5    | 40.0<     | 10 | 142.3* |
| 5 | 0.0005 | 32.6 ± 0.6 | 2 | 116.0 |
|   | 0.005  | 36.1 ± 0.5 | 6 | 128.5 |
|   | 0.05   | 38.2 ± 0.4 | 8 | 135.9* |
|   | 0.5    | 39.2 ± 0.3 | 9 | 139.5* |
| Control | — | 28.1 ± 0.2 | 0 | 100 |

Note: The symbol "*" means that the value is statistically significant with a significance level of 5% or lower with respect to control.

As is evident from the results in Table 1, all of the compounds 1–5 exerted a strong effect on the prolongation of life of mice with a mouse carcinoma when administered with 0.05 μg/mouse/shot or more of either of the compounds 1–5.

Experiment 3

Antitumor Activity by the Inhibition of Tumor Growth

Based on the data of Experiment 2, a minimum dose of the compounds 1–5 to a nude mouse was estimated to be about (Human Cancer and Nude Mice)", pp. 321–323 (1982), published by Ishiyaku Publishers, Inc., Tokyo, Japan, and the percentage surviving (%) on the 35th day after the transplantation was calculated. The results were in Table 2.

TABLE 2

| Tumor cell | Average tumor weight, on a wet cell basis | Percentage surviving at judgement (%) |
|---|---|---|
| HLC-1 cell (lung cancer) | 0.124 ± 0.06 (1.25 ± 0.81) | 100 (71.4) |
| HGC-27 cell (gastric cancer) | 0.35 ± 0.09 (1.86 ± 0.64) | 100 (85.7) |
| Hep G2 cell (cancer of liver) (ATCC HB 8065) | 0.18 ± 0.02 (2.06 ± 0.85) | 100 (42.8) |

TABLE 2-continued

| Tumor cell | Average tumor weight, on a wet cell basis | Percentage surviving at judgement (%) |
| --- | --- | --- |
| HeLa cell (uterine cancer) (ATCC CCL 2) | 0.54 ± 0.06 (1.36 ± 0.61) | 100 (100) |
| RPMI 4788 cell (colon cancer) (FERM BP-2429) | 0.21 ± 0.03 (2.95 ± 1.36) | 100 (71.4) |
| WiDr cell (rectum cancer) (ATCC CCL 218) | 0.36 ± 0.02 (1.83 ± 0.85) | 100 (85.7) |
| KB cell (rhinopharynx cancer) (ATCC CCL 17) | 0.54 ± 0.03 (2.12 ± 0.96) | 100 (42.8) |
| Hep-2 cell (thyroid gland cancer) (ATCC CCL 23) | 0.81 ± 0.65 (2.16 ± 1.31) | 100 (42.8) |
| G-361 cell (malignant melanoma) (ATCC CRL 1424) | 0.36 ± 0.02 (1.96 ± 0.98) | 100 (57.1) |
| HL-60 cell (leukemia) (ATCC CCL 240) | 0.18 ± 0.03 (1.43 ± 0.08) | 100 (100) |
| U-937 cell (lymphoma) (ATCC CRL 1593) | 0.25 ± 0.02 (0.99 ± 0.81) | 100 (85.7) |

Note: The numerals in the parentheses show the average tumor weight, on a wet cell basis, and the percentage surviving when judged in the control group.

As is evident from the results in Table 2, the compound 2 exerted a strong antitumor effect with only a relatively low dose on human malignant tumors such as human lung cancer, gastric cancer, cancer of liver, uterine cancer, colon cancer, rectum cancer, rhinopharynx cancer, thyroid gland cancer, malignant melanoma, leukemia, and lymphoma, and attained a desired percentage surviving on the 35th day after the transplantation of human malignant tumors. Although the data is not shown, similar results were obtained from the experiments using the compounds 1 and 3–5.

Experiment 4

Acute Toxicity Test ddy Mice, 10–20 g weight each, were grouped in a group of 10 mice, then injected intraperitoneally or administered orally using a stomach tube with a physiological saline containing a prescribed amount of either of the compounds 1–5, obtained by the method in Experiments 1-1 and 1-2, and 5% by weight of gum arabic. Thereafter, the mice were observed for 7 days to check the death number, then the $LD_{50}$ was calculated by the Van der Vaerden's Planimetry.

As a result, the $LD_{50}$ of the compounds 1–5 was 200 mg/kg mouse or more independently of their administration routes. Considering in connection with the result and the fact that 3-[4-hydroxy-3,5-bis(3-methyl-2-butenyl)phenyl]-2-propenoic acid and its salts exert a desired effect with a dose of several Ng/shot or more, the present antitumor agent is extremely safe.

The following examples explain the present invention in more detail:

EXAMPLE 1

Tablet

Five types of tablets, comprising per tablet 0.1 mg of either of the compounds 1–5 obtained by the methods in Experiments 1-1 and 1-2, 79.9 mg lactose, 62.5 mg corn starch, 7.5 mg sucrose fatty acid ester, were prepared in a conventional manner. In the case of preparing gastric coated- and enteric coated-tablets, the above tablets were respectively coated with 5% and 10% by weight of hydroxypropyl methyl cellulose, then sugar coated.

These tablets can be selectively used as a therapeutic agent for human malignant tumors including gastric cancer, lung cancer, cancer of liver, uterine cancer, breast cancer, colon cancer, rectum cancer, and malignant melanoma.

EXAMPLE 2

Capsule

Five types of tablets, comprising per tablet 0.2 mg of either of the compounds 1–5 obtained by the methods in Experiments 1-1 and 1-2, 146.8 mg lactose, and 3.0 mg sucrose fatty acid ester, were prepared in a conventional manner.

These tablets can be selectively used as a therapeutic agent for human malignant tumors including gastric cancer, lung cancer, cancer of liver, uterine cancer, breast cancer, colon cancer, rectum cancer, and malignant melanoma.

EXAMPLE 3

Injection

Five types of injections were prepared by mixing 5 g sodium bicarbonate and 5 mg of either of the compounds 1–5 obtained by the methods in Experiments 1-1 and 1-2, and injecting 0.1 g aliquots of each resulting solution into sterile glass containers.

These injections are the types of which are used by dissolving in solvent before use and can be selectively used as a therapeutic agent for human malignant tumors including gastric cancer, lung cancer, cancer of liver, uterine cancer, breast cancer, colon cancer, rectum cancer, and malignant melanoma.

EXAMPLE 4

Agent for External Use

Five types of agents for external use, containing as an effective ingredient 5 mg/g of either of the compounds 1–5 obtained by the methods in Experiments 1-1 and 1-2, were prepared by well mixing the effective ingredient and a small amount of liquid paraffin, and adding petrolatum to each resulting mixture.

These agents can be selectively used as a therapeutic agent for human malignant tumors including skin carcinoma, breast cancer, and lymphoma.

EXAMPLE 5

Powder

Five types of powders containing per dose 499.7 mg sodium bicarbonate and 0.3 mg of either of the compounds 1–5 obtained by the methods in Experiments 1-1 and 1-2.

These powders can be selectively used as a therapeutic agent for human malignant tumors including gastric cancer, lung cancer, cancer of liver, uterine cancer, breast cancer, colon cancer, rectum cancer, and malignant melanoma.

EXAMPLE 6

Suppository

Five types of suppositories containing per dose 0.3 mg of either of the compounds 1–5 obtained by the methods in Experiments 1-1 and 1-2, 1,280 mg polyethylene glycol #1000, and 319.7 mg polyethylene glycol #4000.

These suppositories can be advantageously used as a therapeutic agent for human malignant tumors including colon and rectum cancers.

As is described above, the present invention was made based on the finding that 3-[4-hydroxy-3,5-bis(3-methyl-2-butenyl)phenyl]-2-propenoic acid and its salts, which are prepared from physiologically acceptable cations and 3-[4-hydroxy-3,5-bis(3-methyl-2-butenyl)phenyl]-2-propenoic acid, exert a strong antitumor activity on human malignant tumors. Since 3-[4-hydroxy-3,5-bis(3-methyl-2-butenyl) phenyl]-2-propenoic acid is found in and isolated from the natural world and other compounds are prepared therefrom, they are safer than artificially produced compounds. Therefore, the present antitumor agent containing one or more of these 3-[4-hydroxy-3,5-bis(3-methyl-2-butenyl) phenyl]-2-propenoic acid and its salts as an effective ingredient can be advantageously used to treat human malignant tumors without inducing serious side effects.

The present invention with these Outstanding effect is a significant invention which greatly contributes to this field.

While there has been described what is at present considered to be the preferred embodiments of the invention, it will be understood the various modifications may be made therein, and it is intended to cover in the appended claims all such modifications as fall within the true spirits and scope of the invention.

We claim:

1. A method for treating human malignant tumors, which comprises administering to a patient in need thereof an effective amount of an antitumor agent comprising a pharmaceutically-acceptable carrier and as an effective ingredient at least one member selected from the group consisting of sodium, potassium, calcium, magnesium and ammonium salts of 3-[4-hydroxy-3,5-bis(3-methyl-2-butenyl)phenyl]-2-propenoic acid, said human malignant tumors being colon cancer, rectum cancer, gastric cancer, thyroid gland cancer, lingual cancer, bladder cancer, choriocarcinoma, cancer of liver, uterine cancer, prostatic cancer, pharyngeal cancer, lung cancer, breast cancer, malignant melanoma, Kaposi sarcoma, brain tumor, neuroblastoma, ovarian tumor, testicular tumor, osteosarcoma, pancreatic cancer, renal carcinoma, hupernephroma, angioendothelioma, leukemia and lymphoma.

2. The method of claim 1, wherein said antitumor agent contains at least 0.01% by weight of the effective ingredient.

3. The method of claim 1, wherein the effective ingredient is administered to a patient suffering from human malignant tumor at a dose of about one µg to 10 mg of the effective ingredient, 1–4 shots per day or 1–5 shots per week.

* * * * *

UNITED STATES PATENT AND TRADEMARK OFFICE
CERTIFICATE OF CORRECTION

PATENT NO. : 5,710,179
DATED : Jan. 20, 1998
INVENTOR(S) : Shigeyuki Arai et al.

It is certified that error appears in the above-identified patent and that said Letters Patent is hereby corrected as shown below:

Cover page, column 1, line [30], delete Apr. and insert therefor --July--.

Signed and Sealed this

Second Day of June, 1998

Attest:

BRUCE LEHMAN

Attesting Officer

Commissioner of Patents and Trademarks